US010939986B2

(12) United States Patent
Chen et al.

(10) Patent No.: US 10,939,986 B2
(45) Date of Patent: Mar. 9, 2021

(54) INFERIOR VENA CAVA FILTER

(71) Applicant: SHENZHEN KYD BIOMEDICAL TEHCNOLOGY CO. LTD., Shenzhen (CN)

(72) Inventors: YiLong Chen, Shenzhen (CN); Wei Huang, Shenzhen (CN); Xiangqian Zhao, Shenzhen (CN)

(73) Assignee: SHENZHEN KYD BIOMEDICAL TEHCNOLOGY CO. LTD., Shenzhen (CN)

( * ) Notice: Subject to any disclaimer, the term of this patent is extended or adjusted under 35 U.S.C. 154(b) by 137 days.

(21) Appl. No.: 16/097,066

(22) PCT Filed: Apr. 18, 2017

(86) PCT No.: PCT/CN2017/080892
§ 371 (c)(1),
(2) Date: Oct. 26, 2018

(87) PCT Pub. No.: WO2017/186025
PCT Pub. Date: Nov. 2, 2017

(65) Prior Publication Data
US 2019/0105146 A1    Apr. 11, 2019

(30) Foreign Application Priority Data
Apr. 28, 2016  (CN) .......................... 201610273051.0

(51) Int. Cl.
*A61F 2/01*    (2006.01)
(52) U.S. Cl.
CPC .................. *A61F 2/01* (2013.01); *A61F 2/011* (2020.05); *A61F 2002/016* (2013.01);
(Continued)

(58) Field of Classification Search
CPC .................. A61F 2/01; A61F 2002/011; A61F 2002/016; A61F 2230/005;
(Continued)

(56) References Cited

U.S. PATENT DOCUMENTS 5,324,304 A   6/1994  Rasmussen
7,279,000 B2  10/2007 Cartier et al.
(Continued)

FOREIGN PATENT DOCUMENTS

AU   2017255547 B2   3/2020
CN      2394594 Y    9/2000
(Continued)

OTHER PUBLICATIONS

Examination Report No. 2 in corresponding Australian Application No. 2017255547, dated Nov. 11, 2019.
(Continued)

*Primary Examiner* — Diane D Yabut
(74) *Attorney, Agent, or Firm* — Leason Ellis LLP

(57) ABSTRACT

An inferior vena cava filter comprises a recovery hook (1), a connection component (12), and multiple supporting rods. The connection component (12) is disposed below the recovery hook (1), and a component connected to a push device is disposed in the connection component. Multiple first supporting rods (4) are divided from the lower part of the connection component (12). One second supporting rod (2) and two third supporting rods (5) are divided from the far end of each first supporting rod (4). One part of the far end of the second supporting rod (2) is bent to form a hook shape. The third supporting rods (5) continue to extend downwards. When expanded, the third supporting rods (5) and the third supporting rods (5) divided from the first supporting rods (4) extend in an inner arc shape, and the lower ends of the adjacent two third supporting rods (5)

(Continued)

divided from the adjacent two first supporting rods (4) get close. When expanded, the supporting rods form a filtering net shape as a whole.

14 Claims, 6 Drawing Sheets

(52) U.S. Cl.
CPC . *A61F 2230/005* (2013.01); *A61F 2230/0067* (2013.01); *A61F 2230/0071* (2013.01)

(58) Field of Classification Search
CPC ...... A61F 2230/0067; A61F 2230/0071; A61F 2/0105; A61F 2/0108; A61F 2/011; A61F 2/012; A61F 2/013; A61F 2/014; A61F 2002/015; A61F 2002/018
See application file for complete search history.

(56) References Cited

U.S. PATENT DOCUMENTS

| | | | | |
|---|---|---|---|---|
| 7,338,512 | B2* | 3/2008 | McGuckin, Jr. | A61F 2/01 606/200 |
| 2002/0193828 | A1* | 12/2002 | Griffin | A61F 2/01 606/200 |
| 2006/0079928 | A1* | 4/2006 | Cartier | A61F 2/01 606/200 |
| 2010/0049239 | A1 | 2/2010 | McGuckin, Jr. et al. | |
| 2010/0150954 | A1 | 6/2010 | Miller et al. | |
| 2013/0006294 | A1* | 1/2013 | Kashkarov | A61L 31/148 606/200 |
| 2016/0097066 | A1 | 4/2016 | Nicaud et al. | |

FOREIGN PATENT DOCUMENTS

| | | |
|---|---|---|
| CN | 103007361 A | 4/2013 |
| CN | 103027763 A | 4/2013 |
| CN | 103031523 A | 4/2013 |
| CN | 203841850 U | 9/2014 |
| CN | 104434339 A | 3/2015 |
| CN | 103815984 B | 1/2016 |
| CN | 105361974 A | 3/2016 |
| EP | 3449870 A1 | 3/2019 |
| WO | WO 2006036457 A2 | 4/2006 |
| WO | WO 2008051294 A2 | 5/2008 |
| WO | WO 2017/186025 | 11/2017 |

OTHER PUBLICATIONS

International Search Report and Written Opinion. in corresponding PCT Application No. PCT/CN2017/080892, dated Jul. 24, 2017.
Canadian Office Action in corresponding Canadian Application No. 3,022,010, dated Sep. 16, 2019.
Indonesian Office Action in corresponding Indonesian Application No. PID201809645, dated May 6, 2020.

* cited by examiner

INFERIOR VENA CAVA FILTER

CROSS-REFERENCE TO RELATED PATENT APPLICATIONS

This application is a U.S. National Phase Application under 35 U.S.C. § 371 of International Patent Application No. PCT/CN2017/080892, filed Apr. 18, 2017, and claims the priority of Chinese Application No. 201610273051.0, filed Apr. 28, 2016, all of which are incorporated by reference in their entireties. The International Application was published on Nov. 2, 2017 as International Publication No. WO 2017/186025 A1.

TECHNICAL FIELD OF THE INVENTION

The invention relates to a medical instrument, in particular a retrievable inferior vena cava filter which has good filtration effect against thrombus and can be secured stably with prolonged implantation time.

BACKGROUND OF THE INVENTION

Deep vein thrombosis (DVT) of the lower extremity is a common clinical disease, and the incidence is increasing year by year. The pathogenic factors include obesity, the history of venous thrombosis, varicosity, abnormal coagulation mechanism, diabetes, oral contraceptives, trauma, child delivery and so on, which are all related to the slow blood flow, the increase of blood viscosity and the damage of the vascular intima. The most serious complication of DVT is pulmonary embolism (PE) caused by the detachment of thrombus. PE has rapid onset and rapid progression, and the patient with pulmonary thromboembolism usually dies within the first hour of onset. In addition, post PE syndromes (such as chest tightness and shortness of breath, which become aggravated by activity or tiredness, and pulmonary hypertension) affect daily life and work. Epidemiological survey in recent years shows that PE occurs in approximately 60% to 70% of patients with DVT of lower extremity. Taking the United States as an example, the annual incidence of PE is 750 thousand to 900 thousand, and the annual death toll is 120 thousand to 150 thousand.

Because of the high incidence and risk characteristics (rapid onset and rapid death) of PE in patients with DVT of lower extremity, preventing DVT and concurrent PE is the key to reduce mortality. Anticoagulation is currently used as the main treatment for DVT and prevention of PE domestically and abroad, including low molecular weight heparin therapy and subsequent oral warfarin treatment. But studies have shown that PE still occurs in up to 33% of patients under strict anticoagulant therapy. Because of the contraindications of anticoagulant therapy (such as patients with the history of trauma or surgery with high bleeding risk, hemorrhagic stroke, central nervous system tumor, and patients with bleeding tendency and coagulation dysfunction), some patients with DVT and/or PE are not eligible for anticoagulant therapy. In case of oral warfarin anticoagulant therapy, the drug can affect the development of the fetus through the placenta. In these circumstances, placing VCF in the inferior vena cava through interventional procedure is the only way to prevent PE.

At present, the clinical VCF is a kind of instrument which is made by weaving of metal wires or laser engraving of a piece of metal, and which is put into the inferior vena cava via the femoral vein or right internal jugular vein by a special conveying device, so as to form a network protective structure to block the large thrombus in the blood flow. Studies have shown that a small thrombus is difficult to cause a pulmonary thromboembolism. When the thrombus diameter is larger than 7.5 mm, patients with pulmonary embolism can be in a life crisis. Studies have shown that a small thromboembolus is unlikely to cause a pulmonary thromboembolism, and only the thromboembolus with the diameter larger than 7.5 mm can be life-threatening to the patients with pulmonary embolism. VCF itself has no therapeutic effect on DVT of lower extremity, and its significance is to prevent PE from occurring when the larger embolus falls off and blocks the pulmonary artery. Clinical retrospective analysis showed that the placement of VCF could effectively prevent PE. The incidence of PE in DVT patients decreased from 60%-70% to 0.9%-6%, and the incidence of fatal PE was reduced to 0.7%-4%. At present, the clinical application of VCF is mainly divided into the first generation (permanent type) VCF and the second generation (retrievable and temporary type) VCF.

Once the first generation (permanent type) VCF is imbedded into the inferior vena cava, its position could not be adjusted, and it could not be removed. The long term placement can result in shift of filter, recurrent PE and the inferior vena cava obstruction. Decousus randomized study found that the recent incidence of PE decreased after the implantation of the filter, but the reoccurrence of PE caused by deep venous thrombosis increased significantly in recent 2 years. Obergassel and others found that of 2646 patients who had used permanent VCF, longer placement time had higher incidents of complications, such as 41% with penetrating blood vessel, 26% with displacement and 30% with thrombotic occlusion. According to the invention in CN101147705A, ceramic membrane is used to improve the performance of the surface of nickel-titanium alloy, improve the biocompatibility of the metal and promote the rapid climbing of the endothelial cells, so as to reduce the formation of thrombus caused by these factors. However, the permanent filter may cause patients to take anticoagulant drugs all the time and cause other complications. Therefore, in the mid-1980s, an experimental study on retrievable VCF was started.

The second generation VCF includes retrievable VCF and the temporary VCF. The temporary VCF is still attached to the percutaneous catheter or guide wire after being imbedded into the inferior vena cava. It is easy to take out the filter at any time, but it has the disadvantages of the risk of infection, increasing the risks caused by puncture vein injury, bleeding and thrombosis, and bringing inconvenience to the patient's action. At present, the temporary VCF is rarely used. After the retrievable VCF is imbedded into the inferior vena cava, if the patient has passed the risk of thrombosis, a special recovery system can be used to recover VCF from the inferior vena cava through the internal jugular vein or femoral vein by the interventional method, thus avoiding a series of complications caused by long-term indwelling. If necessary, it can remain in the original position as permanent VCF without replacement. Clinical studies have shown that the effect of retrievable VCF and permanent VCF on preventing pulmonary embolism is the same. At present, most scholars advocate taking out the retrievable VCF within 10 days after imbedding, because it has been confirmed by animal experiments that the imbedded filter can be attached by the vascular endothelial cells of the inferior vena cava wall which causes endothelialization that is basically completed within 7~10 days.

Clinically, for some patients, such as those with pelvic fractures, it is necessary to place the VCF inside the inferior vena cava for 2-3 months, so as to achieve the effect of preventing pulmonary embolism in the middle and long term. At present, such effect can be achieved only by permanently retaining the filter in human body. The inventions in CN103031523A and CN103007361A indicate that the cytotoxic copper metal is plated on the VCF surface to delay the attachment of vascular endothelial cells on the surface of the filter. However, the long-term toxicity of heavy metal copper can cause serious adverse effects on the human body, and induce secondary thrombosis on the surface of the filter, causing the vascular occlusion and affecting the blood flow. According to the invention in CN103027763A, a polymer coating which is not conducive to the growth of endothelial cells is used on the surface of the inferior vena cava filter to delay the endothelial cell attachment. The disadvantage is that the cytotoxic polymer coating is not only toxic to the endothelial cells, but its toxicity can also induce secondary thrombosis on the surface of the filter, resulting in vascular occlusion.

In addition, Chinese patent CN105361974A discloses an inferior vena cava filter with a double-layer structure and a grid filter plate, which can filter the thrombus better and enhance the self-centered function of the device. It takes into account the balance between the fixed and retrievable key effects. However, an umbrella shaped support pole structure of the filter is tightly attached to the vascular wall, which can result in easy endothelialization. The time of implanting inside the blood vessel is still limited. American patent US 20100160954A1 discloses a removable vena cava filter with two layers of support sites, which prevents the filter from moving with the blood flow of the blood vessel, and also from attaching to the vascular wall along the length direction of the support pole, such that the ends of the support poles contact the vascular wall, avoiding the endothelialization of the filter. However, the fixed effect of the support sites of the filter is not adequate, so it lacks good self centering.

The presently recognized ideal vena cava filter must have the following features: ①it does not cause secondary thrombosis and has good biocompatibility; ②it can effectively capture exfoliated thrombus, but does not affect venous blood return; ③it can be safely and reliably secured to the wall of the inferior vena cava and is not easy to move; ④the filter conveyer system has a fine diameter, with a simple release mechanism; ⑤it has good centering function and is easy to be tightened by a capture device for facilitating retrieval; ⑥it does not have ferromagnetism and does not affect magnetic resonance imaging; ⑦it has good mechanical stability and is not easy to deform, break, and disintegrate; ⑧there is no serious complication; and ⑨it can be retrieved, even after implantation for 2~3 months. With the continuous improvement of the filter, some filters have most of above features, but so far, none of the filters could meet all of the above features at the same time.

Therefore, the aim of invention is to develop a filter which is easy to deploy, with high efficiency of capturing thrombus without affecting the blood flow of the inferior vena cava. The filter should be safely fixed to the inferior vena cava wall, has good centering capability and is easy to be tightened by the capture device for recovery. More importantly, it should be a retrievable inferior vena cava filter with prolonged implantation time.

SUMMARY OF THE INVENTION

Considering the defects of the prior art, the aim of the invention is to develop a filter which is easy to deploy, with high efficiency of capturing thrombus without affecting the blood flow of the inferior vena cava. The filter can be safely fixed to the inferior vena cava wall, has good centering capability and is easy to be tightened by a capture device for retrieval. More importantly, it is a retrievable inferior vena cava filter with prolonged implantation time. The invention solves the above technical problems by the specific technical solutions as follows.

An inferior vena cava filter, comprising: a retrieval hook 1, a connecting part 12 and a plurality of support poles. The connecting part 12 is arranged under the retrieval hook 1. The inside of the connecting part is provided with a component connected with a push device. The lower part of the connecting part 12 is divided into a plurality of first support poles 4, a distal end of each of which is divided into a second support pole 2 and two third support poles 5. A part of distal end of the second support pole 2 is bent upwards or downwards, forming a crook form. The third support poles 5 extending downwards continuously. When expanded, two third support poles 5 divided from the same first support pole 4 stretch in an arc that bends inward, and lower parts of two adjacent third support poles 5 divided from two adjacent first support poles 4 are close together. When expanded, all support poles are respectively stretching out and form a filter net as a whole.

Preferably, the plurality of first support poles 4 are evenly divided from the lower part of the connecting part 12 as the center. Third support poles 5 divided from the same first support pole 4 may be divided from the first support pole 4 as the center. The proximal end of the second support pole 2 and the first support poles 4 which the second support poles are divided from are basically in the same straight line.

When expanded, two third support poles 5 divided from the same first support pole 4 of the invention stretch in an arc that bends inward. Such design can reduce the contact area between the support poles and the inner surface of the blood vessel and reduce the possibility of endothelialization. At the same time, the lower parts of two adjacent third support poles 5 divided from two adjacent first support poles 4 are close together, such that the filter has more multi-point support and can stabilize configuration of the filter in the blood vessel. When the filter slightly misalign inside the blood vessel, multiple endpoints are attached to the vascular wall to prevent further tilting, so as to keep the centrality of the filter in the blood vessel.

Preferably, the numbers of the first support poles 4 and the second support poles 2 are respectively between 4 and 8 and are more preferably 6. Preferably, the number of the third support poles 5 is between 8 and 16 and is more preferably 6.

The preferable lengths of the first support poles 4 and the third support poles 5 are respectively 8-16 mm and 10-16 mm.

The above numbers of the support poles are provided according to a large number of experiments. A regular filter net shape can be formed by the even distribution of a plurality of support poles. Too few support poles are not conducive to the stability of the filter body in the blood vessel, while too many support poles are difficult to process and waste materials at the same time. The length range of the first support poles 4, the third support poles 5 and the second support poles 2 makes the filter body more suitable for placing the inferior vena cava between the renal vein and the iliac vein and prevents the lower extremity thrombus from ascending and entering the lungs to cause pulmonary embolism.

More preferably, the lower parts of two adjacent third support poles 5 divided from two adjacent first support poles 4 are close together at the position which is 10-15 mm from the ends of the third support poles. The ends are slightly branched and splayed, so as to have better stability after the implantation of the filter.

The length of a bending part at the distal end of the second support poles 2 is 4-20 mm. The curvature radius of bending is 3-10 mm, and the bending angle is 90-270 degrees.

By setting the above shape, the second support poles 2 can prevent the filter from migrating when the blood is flowing, which is preferably bent upwards or downwards to form a crook type support pole. The crook type support pole of the structure can more firmly hook the inner wall of the blood vessel and further improve the self centering of the filter body.

Both of the ends 3 and 6 of the second support poles 2 and the third support poles 5 are the spherical round heads and attached to the inner wall of the blood vessel.

The ends of all support poles are spherical round heads, supporting the blood vessel and preventing puncturing the vascular wall. The second support poles 2 are bent upwards or downwards and the third support poles 5 are arranged below which allow the filter to have two layers of sites contacting the blood vessel, such that the filter has better self centering to prevent the filter from tilting after implantation. Such design also greatly reduces the contact area between the device and the inner surface of the blood vessel, which increases the difficulty of the endothelial cells to attach and delays the time of covering the support poles by endothelial tissue. Even with endothelialization, the design of a plurality of support poles makes it easy to extract the support poles from the endothelial tissue under the action of an upward force, so as to reduce the damage to the blood vessel when the device is retrieved.

Preferably, the diameter of the spherical round head of the ends 3 is about 25-45 mm; and preferably the diameter of the spherical round head of the ends 6 is about 35-65 mm.

The diameter of the spherical round head at the end of the support pole should not be too small, otherwise it will affect the supporting action on the inner surface of the blood vessel. Too large diameter of the round head is difficult for extracting the support pole from the endothelial tissue. because the second support pole 2 is easier to be covered by the endothelial tissue. The circle diameter of the endpoint 3 should be smaller, such that the contact area between said endpoint and the vascular wall is reduced, which can delay the time of covering the support pole 2 by the endothelial tissue.

When the inferior vena cava filter is expanded, the end of the second support pole 2 is the endpoint 3. The distance D1 between two symmetrical end endpoints 3 is 5-10 mm larger than the diameter of the blood vessel. The end of the third support pole 5 is the endpoint 6, and the distance D2 between two symmetrical end endpoints 6 is 15-25 mm larger than the diameter of the blood vessel.

According to the design of the invention, both D1 and D2 are larger than the diameter of the blood vessel and D2 is larger than D1, which makes the filter body more stable in the blood vessel. This further prevents the migration of the filter.

Another preferable alternative of the invention is that the inferior vena cava filter does not include the second support pole 2, or the second support pole 2 is not bent.

The inferior vena cava filter is preferably formed by the laser cutting of nickel-titanium alloy tube, and the filter net structure of the filter adopts the design of single-layer filter net.

The vena cava filter of the invention is formed by the laser cutting of nickel-titanium alloy tube which has diamagnetism and does not affect the magnetic resonance imaging. The vena cava filter adopts the design of single-layer filter net, so it has excellent mechanical stability, is not easy to break and fall apart, and can maintain structural integrity.

The connection between the connecting part 12 and a push device can be selected from a threaded connection, buckle connection and trap connection. The push device is preferably a push rod.

In case of the threaded connection, the connecting nut of the connecting part and filter body can be made from the same material.

When the filter body is made from a nickel-titanium alloy tube, the connecting nut is also made from the nickel-titanium alloy, which avoids introducing different kinds of materials in the device, so as to avoid the self-corrosion of the filter which damages the mechanical properties of instrument and produces toxic substances. Thus, the filter of the invention is more conducive to prolonging the time of temporary placement or to permanent implanting inside human body.

The terms of "about" and "slightly" concerning the dimension in the invention refer to the size difference or error known to the person skilled in the art, preferably, within ±1 mm, or within ±0.5 mm, or more preferably within ±0.2 mm.

Compared with prior art, the retrievable inferior vena cava filter with prolonged implantation time of the invention has the beneficial effects as follows.

The inferior vena cava filter of the invention can be temporarily placed in the inferior vena cava through interventional procedure to prevent pulmonary embolism caused by the ascending of thrombosis formed in the veins of the lower extremity. The implementation of the invention can prolong the temporary placement time of the inferior vena cava filter in the blood vessel, effectively preventing secondary pulmonary embolism and offering protection during the risk period of pulmonary embolism. After the risk period of thrombosis, the inferior vena cava filter can be removed successfully, so as to avoid permanent implantation of the inferior vena cava filter in the blood vessel and causing subsequent risks and complications of permanent implantation.

The structure of the inferior vena cava filter of the invention provides the filter with two layers of sites contacting the blood vessel, while the design of multiple endpoints greatly reduces the contact area between the device and the inner surface of the blood vessel. This converts the surface-to-surface contact into point-to-point contact, which makes it more difficult for the endothelial cell to attach. This can prolong the time of keeping the inferior vena cava filter in the blood vessel to 2~3 months and is used for keeping the centrality of the filter in the blood vessel.

The inferior vena cava filter of the invention has the structure of two layers of sites contacting the blood vessel, such that the filter has better self centering, and the filter is prevented from tilting after implantation.

The inferior vena cava filter of the invention is designed with multiple poles, which makes it easy to extract the support poles from the endothelial tissue under the action of an upward tension and is convenient for removing operation.

The inferior vena cava filter of the invention is stably secured in the inferior vena cava and is provided with the spherical round heads of the support poles, which can effectively prevent the filter from damaging the vascular wall of the patient.

The product of the invention is formed by the laser cutting of nickel-titanium alloy tube which has diamagnetism and does not affect magnetic resonance imaging.

The product of the invention adopts the design of a single-layer filter net. It has excellent mechanical stability, is not easy to break and fall apart, and can maintain structural integrity.

In the figures: 1—retrieval hook; 2, 4, 5, 10—support poles; 3, 6—spherical round head; 7—inferior vena cava; 8—iliac vein; 9—renal vein; 11—branching point of support pole; 12—connecting part.

SPECIFIC IMPLEMENTATIONS

The invention is further detailed with reference of specific examples and drawings. The content of the invention is not limited to the embodiments.

Embodiment 1

Figure 1:
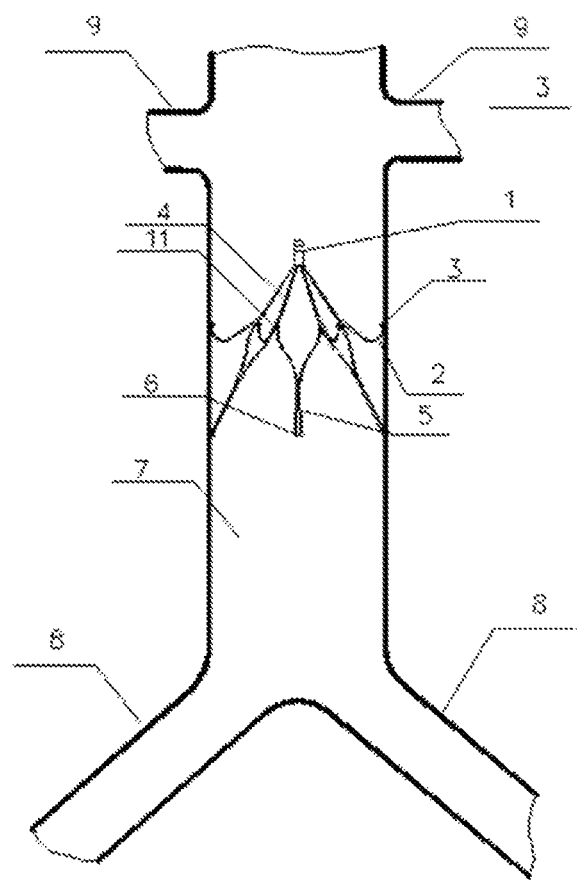
FIG. 1 is a schematic diagram of the inferior vena cava filter of the invention inside the blood vessel.
Figure 2:
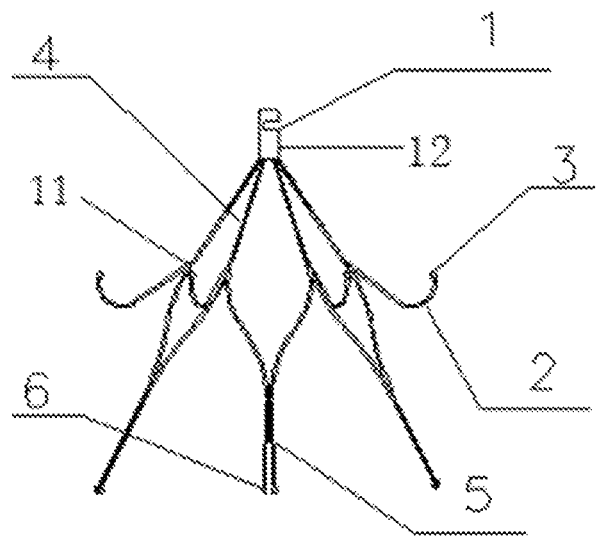
FIG. 2 is a front view of the first to fourth embodiments of the inferior vena cava filter of the invention.
Figure 4:
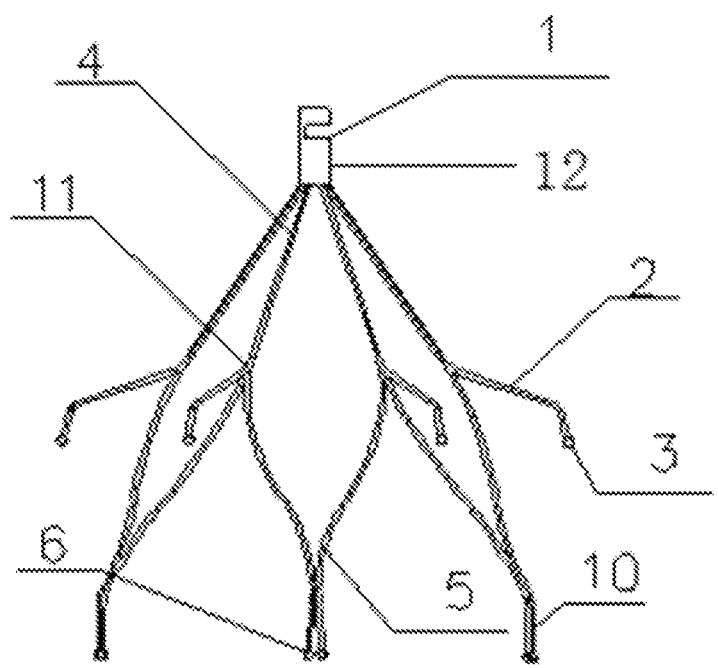
FIG. 4 is a front view of the fifth embodiment of the inferior vena cava filter of the invention.

As shown in FIG. 1, the vena cava filter involved in the invention is positioned in the inferior vena cava 7 between the renal vein 9 and the iliac vein 8 through the interventional method to prevent the lower extremity thrombus from ascending and entering the lungs and causing pulmonary embolism. As shown in FIG. 2 or 4, we adopt the design of single-layer filter net, which has excellent mechanical stability, is not easy to break and fall apart, and can maintain structural integrity. The retrieval hook 1 is used for removing the filter. The connecting part 12 is arranged under the retrieval hook 1. The inside of the connecting part is provided with a component connected with the push device. The connection between the connecting part and the push device can be selected from a threaded connection, buckle connection and trap connection. The lower end of the connecting part 12 is divided into a plurality of first support poles 4, and each support pole 4 is divided into one second support pole 2 and two third support poles 5 at the position of 11. The distal end of the support pole 2 is bent upwards or downwards to form a crook form and support the blood vessel. The third support poles 5 extend downwards continuously. Two third support poles 5 divided from the same first support pole 4 stretch in an arc that bends inward. The lower parts of two adjacent third support poles 5 divided from two adjacent first support poles 4 are close together. When expanded, all support poles respectively stretch and form a filter net as a whole.

Embodiment 2

Figure 3:
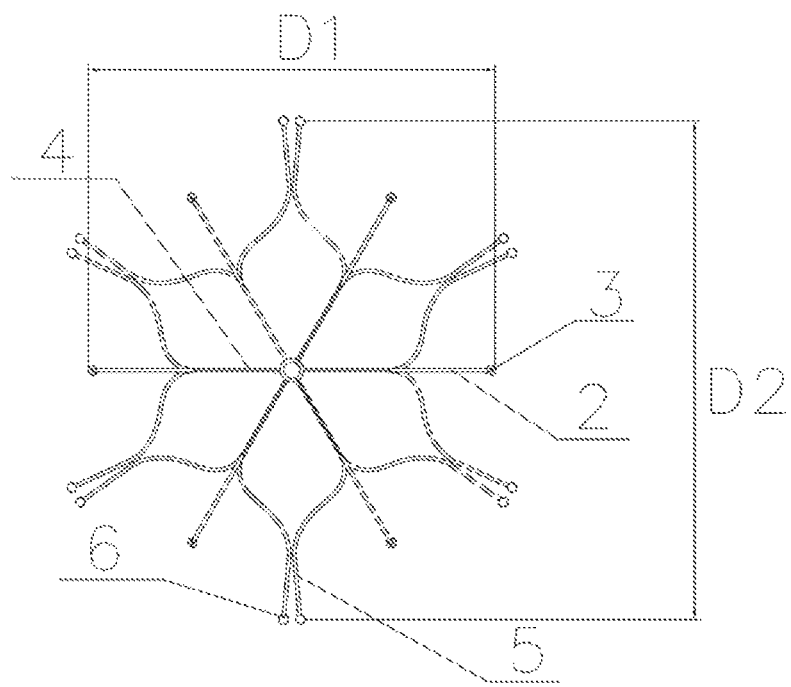
FIG. 3 is a top view of the second to fourth embodiments of the inferior vena cava filter of the invention when expanded.

As shown in FIG. 1, the vena cava filter involved in the invention is positioned in the inferior vena cava 7 between the renal vein 9 and the iliac vein 8 through the interventional method to prevent the lower extremity thrombus from ascending and entering the lungs and causing pulmonary embolism. As shown in FIG. 2, we adopt the design of a single-layer filter net, which has excellent mechanical stability, is not easy to break and fall apart, and can maintain structural integrity. As shown in FIG. 2, the vena cava filter of the embodiment is formed by the laser cutting of a nickel-titanium alloy tube which has diamagnetism and does not affect the magnetic resonance imaging. The retrieval hook 1 is used for removing the filter. The connecting part 12 is arranged under the retrieval hook 1. The inside of the connecting part is provided with the component connected with a push device. The connection between the connecting part and the push device can be selected from the threaded connection, buckle connection and trap connection. In case of the threaded connection, the connecting nut is also made from the nickel-titanium alloy, which avoids introducing different kinds of materials in the device, so as to avoid self-corrosion of the filter which damages the mechanical properties of the device and produces toxic substances. Thus, the filter of the embodiment is more conducive to prolonging the time of temporary placement and ca be used for permanent implanting inside a human body. As shown in FIGS. 2 and 3, the lower end of the connecting part 12 is divided into a plurality of first support poles 4. The support poles 4 are evenly divided from the lower part of the connecting part 12 as the center. Each support pole 4 is divided into one second support pole 2 and two third support poles 5 at the position of 11. The distal end of the support pole 2 is bent upwards to form a crook form and contacts the blood vessel. The proximal end of the second support pole 2 and the first support pole 4 which the second support pole is divided from are basically in the same straight line. The third support poles 5 extend downwards continuously. Two third support poles 5 divided from the same first support pole 4 are divided from the first support pole 4 as the center and stretch in an arc that bends inward. The lower parts of two adjacent third support poles 5 divided from two adjacent first support poles 4 are close together. When expanded, all support poles respectively stretch out and form a filter net as a whole. As shown in FIG. 3, when the filter body is expanded, the distance D1 between two symmetrical endpoints 3 is less than the distance D2 between two symmetrical endpoints 6.

Embodiment 3

As shown in FIG. 1, the vena cava filter involved in the invention is positioned in the inferior vena cava 7 between the renal vein 9 and the iliac vein 8 through the interventional method to prevent the lower extremity thrombus from ascending and entering the lungs and causing pulmonary embolism. As shown in FIG. 4, we adopt the design of single-layer filter net, which has excellent mechanical stability, is not easy to break and fall apart, and can maintain structural integrity. As shown in FIG. 2, the vena cava filter of the embodiment is formed by the laser cutting of a nickel-titanium alloy tube which has diamagnetism and does not affect the magnetic resonance imaging. The retrieval hook 1 is used for removing the filter. The connecting part 12 is arranged under the retrieval hook 1. The inside of the connecting part is provided with the component connected with a push device. The connection between the connecting part and the push device can be the threaded connection, buckle connection or trap connection. In case of the threaded connection, the connecting nut is also made from the nickel-titanium alloy, which avoids introducing different kinds of materials in the device, so as to avoid the self-corrosion of the filter which damages the mechanical properties of device and produces toxic substances, thus the filter of the invention is more conducive to prolonging the time of temporary placement and can be used for permanent implanting inside a human body. As shown in FIGS. 3 and 4, the lower end of the connecting part 12 is divided into 4-8 first support poles 4, the support poles 4 are evenly divided from the lower part of the connecting part 12 as the center. Each support pole 4 is divided into one second support pole 2 and two third support poles 5 at the position of 11. There are totally 4-8 second support poles 2 and 8-16 third support poles 5. The distal end of the support pole 2 is bent downwards to form a crook form and contacts the blood vessel. The proximal end of the second support pole 2 and the first support poles 4 which the second support pole are divided from are basically in the same straight line. The end endpoint 3 of the support pole 2 is a spherical round head. The third support poles 5 extend downwards continuously. Two third support poles 5 divided from the same first support pole 4 are divided from the first support pole 4 as the center and stretched in an arc that bends inward. The lower parts of two adjacent third support poles 5 divided from two adjacent first support poles 4 are close together. The ends are slightly branched and splayed. The end endpoints 6 of the support poles 5 are spherical round heads contacting the blood vessel. When expanded, all support poles respectively stretch out and form a filter net as a whole. As shown in FIG. 3, when the filter body is expanded, the distance D1 between two symmetrical endpoints 3 is less than the distance D2 between two symmetrical endpoints 6.

Embodiment 4

As shown in FIG. 1, the vena cava filter involved in the invention is positioned in the inferior vena cava 7 between the renal vein 9 and the iliac vein 8 through the interventional method to prevent the lower extremity thrombus from ascending and entering the lungs and causing pulmonary embolism. As shown in FIG. 2, we adopt the design of single-layer filter net, which has excellent mechanical stability, is not easy to break and fall apart, and can maintain structural integrity. As shown in FIG. 2, the vena cava filter of the embodiment is formed by the laser cutting of a nickel-titanium alloy tube which has diamagnetism and does not affect the magnetic resonance imaging. The retrieval hook 1 is used for removing the filter. The connecting part 12 is arranged under the retrieval hook 1. The inside of the connecting part is provided with the component connected with a push device. The connection between the connecting part and the push device can be the threaded connection, buckle connection or trap connection. In case of the threaded connection, the connecting nut is also made from the nickel-titanium alloy, which avoids introducing different kinds of materials in the device, so as to avoid the self-corrosion of the filter which damages the mechanical properties of device and produces toxic substances, thus the filter of the invention is more conducive to prolonging the time of temporary placement and can be used for permanent implanting inside a human body. As shown in FIGS. 2 and 3, the lower end of the connecting part 12 is divided into 6 first support poles 4 with the length of 8-16 mm. The support poles 4 are evenly divided form the lower part of the connecting part 12 as the center. Each support pole 4 is divided into one second support pole 2 and two third support poles 5 at the position of 11. There are totally 6 second support poles 2 and 12 third support poles 5, each with the length of 10-16 mm. The distal end of the support pole 2 is bent upwards or downwards to form a crook form and contacts the blood vessel. The length of the bending part of the second support pole 2 is 4-20 mm. The curvature radius of bending is 3-10 mm, and the bending angle is 90-270 degrees. The proximal end of the second support pole 2 and the first support poles 4 which the second support pole are divided from are basically in the same straight line. The end 3 of the support poles 2 is a spherical round head with the diameter of 25-45 mm. The third support poles 5 extend downwards continuously. Two third support poles 5 divided from the same first support pole 4 are divided from the first support pole 4 as the center and stretch in an arc that bends inward. The lower parts of two adjacent third support poles 5 divided from two adjacent first support poles 4 are close together at the position which is 10-15 mm apart from the ends of the third support poles. The ends are branched and splayed. The ends 6 of the support poles 5 are spherical round heads with the diameter of 35-65 mm contacting the blood vessel. When expanded, all support poles respectively stretch out and form a filter net as a whole. As shown in FIG. 3, when the filter body is expanded, the distance D1 between two symmetrical endpoints 3 is less than the distance D2 between two symmetrical endpoints 6. D1 is 5-10 mm larger than the diameter of the blood vessel, and D2 is 15-25 mm larger than the diameter of the blood vessel.

Embodiment 5

As shown in FIG. 1, the vena cava filter involved in the invention is positioned in the inferior vena cava 7 between the renal vein 9 and the iliac vein 8 through the interventional method to prevent the lower extremity thrombus from ascending and entering the lungs and causing pulmonary embolism. As shown in FIG. 4, we adopt the design of single-layer filter net, which has excellent mechanical stability, is not easy to break and fall apart, and can maintain structural integrity. As shown in FIG. 4, the vena cava filter of the embodiment is formed by the laser cutting of a nickel-titanium alloy tube which has diamagnetism and does not affect the magnetic resonance imaging. The retrieval hook 1 is used for removing the filter. The connecting part 12 is arranged under the retrieval hook 1. The inside of the connecting part is provided with the component connected with a push device. The connection between the connecting part and the push device can be the threaded connection, buckle connection or trap connection. In case of the threaded connection, the connecting nut is also made from the nickel-titanium alloy, which avoids introducing different kinds of materials in the device, so as to avoid the self-corrosion of the filter which damages the mechanical properties of device and produces toxic substances. Thus, the filter of the invention is more conducive to prolonging the time of temporary placement and can be used for permanent implanting inside a human body. As shown in FIG. 4, the lower end of the connecting part 12 is divided into 4-8 first support poles 4 with the length of 8-16 mm. The support poles 4 are evenly divided form the lower part of the connecting part 12 as the center. Each support pole 4 is divided into one second support pole 2 and two third support poles 5 at the position of 11. There are totally 4-8 second support poles 2 and 8-16 third support poles 5, each with the length of 10-16 mm. The distal end of the support pole 2 is bent downwards to form a subvertical support pole and contacts the blood vessel. The proximal end of the second support pole 2 and the first support poles 4 which the second support pole are divided from are basically in the same straight line, and the end 3 of the support poles 2 is a spherical round head with the diameter of 25-45 mm. The third support poles 5 extend downwards continuously. Two third support poles 5 divided from the same first support pole 4 are divided from the first support pole 4 as the center and stretch in an arc that bends inward. The lower parts of two adjacent third support poles 5 divided from two adjacent first support poles 4 are close together at the position which is 10-15 mm from the ends of the third support poles. The ends are slightly branched and splayed, the lower end 10 of which formed a subvertical support poles 10. The ends 6 of the support poles 5 are spherical round heads with the diameter of 35-65 mm contacting the blood vessel. When expanded, all support poles respectively stretch and form a filter net as a whole.

Embodiment 6

Figure 5:
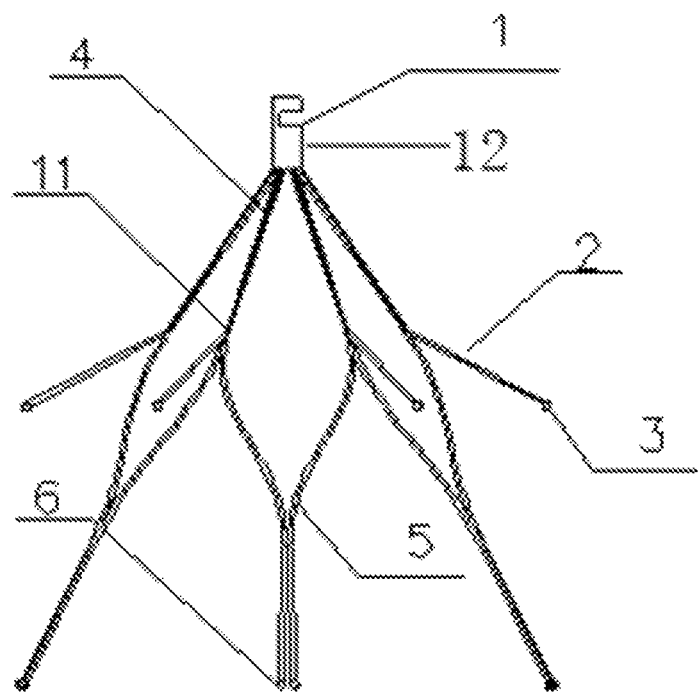
FIG. 5 is a front view of the sixth embodiment of the inferior vena cava filter of the invention.

As shown in FIG. 1, the vena cava filter involved in the invention is positioned in the inferior vena cava 7 between the renal vein 9 and the iliac vein 8 through the interventional method to prevent the lower extremity thrombus from ascending and entering the lungs and causing pulmonary embolism. As shown in FIG. 5, we adopt the design of single-layer filter net. As shown in FIG. 5, the vena cava filter of the embodiment is formed by the laser cutting of a nickel-titanium alloy tube which has diamagnetism and does not affect the magnetic resonance imaging. The vena cava filter has excellent mechanical stability, is not easy to break and fall apart, and can maintain structural integrity. The retrieval hook 1 is used for removing the filter. The connecting part 12 is arranged under the retrieval hook 1. The inside of the connecting part is provided with the component connected with a push device. The connection between the connecting part and the push device can be the threaded connection, buckle connection or trap connection. In case of the threaded connection, the connecting nut is also made from the nickel-titanium alloy, which avoids introducing different kinds of materials in the device, so as to avoid the self-corrosion of the filter which damages the mechanical properties of device and produces toxic substances. Thus, the filter of the invention is more conducive to prolonging the time of temporary placement and can be used for permanent implanting inside a human body. As shown in FIG. 5, the lower end of the connecting part 12 is divided into 4-8 first support poles 4 with the length of 8-16 mm. The support poles 4 are evenly divided form the lower part of the connecting part 12 as the center. Each support pole 4 is divided into one second support pole 2 and two third support poles 5 at the position of 11. There are totally 4-8 second support poles 2 and 8-16 third support poles 5, each with the length of 10-16 mm. The support poles 2 stretch downwards straightly and contact the blood vessel. The proximal end of the second support pole 2 and the first support poles 4 which the second support pole are divided from are basically in the same straight line. The end 3 of the support pole 2 is a spherical round head with the diameter of 25-45 mm. The third support poles 5 extend downwards continuously. Two third support poles 5 divided from the same first support pole 4 are divided from the first support pole 4 as the center and stretch in an arc that bends inward. The lower parts of two adjacent third support poles 5 divided from two adjacent first support poles 4 are close together at the position which is 10-15 mm from the ends of the third support poles. The ends are slightly branched and splayed. The ends 6 of the support poles 5 are spherical round heads with the diameter of 35-65 mm contacting the blood vessel. When expanded, all support poles respectively stretch and form a filter net as a whole.

Embodiment 7

Figure 6:
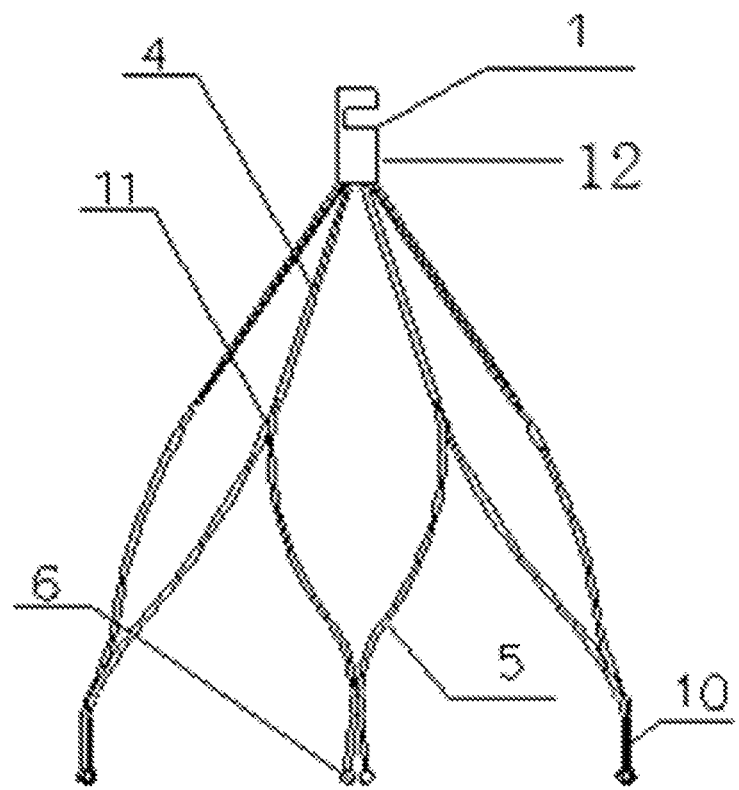
FIG. 6 is a front view of the seventh embodiment of the inferior vena cava filter of the invention.

As shown in FIG. 1, the vena cava filter involved in the invention is positioned in the inferior vena cava 7 between the renal vein 9 and the iliac vein 8 through the interventional method to prevent the lower extremity thrombus from ascending and entering the lungs and causing pulmonary embolism. As shown in FIG. 6, we adopt the design of single-layer filter net. As shown in FIG. 6, the vena cava filter of the invention is formed by the laser cutting of a nickel-titanium alloy tube which has diamagnetism and does not affect the magnetic resonance imaging. The vena cava filter has excellent mechanical stability, is not easy to break and fall apart, and can maintain structural integrity. The retrieval hook 1 is used for removing the filter. The connecting part 12 is arranged under the retrieval hook 1. The inside of the connecting part is provided with a component connected with a push device. The connection between the connecting part and the push device can be the threaded connection, buckle connection or trap connection. In case of the threaded connection, the connecting nut is also made from the nickel-titanium alloy, which avoids introducing different kinds of materials in the device, so as to avoid the self-corrosion of the filter which damages the mechanical properties of device and produces toxic substances. Thus, the filter of the invention is more conducive to prolonging the time of temporary placement and can be used for permanent implanting inside a human body. As shown in FIG. 6, the lower end of the connecting part 12 is divided into 4-8 first support poles 4 with the length of 8-16 mm. The support poles 4 are evenly divided from the lower part of the connecting part 12 as the center. Each support pole 4 is divided into two third support poles 5 at the position of 11. There are totally 8-16 third support poles 5, each with the length of 10-16 mm. The third support poles 5 extend downwards continuously. Two third support poles 5 divided from the same first support pole 4 are divided from the first support pole 4 as the center and stretch in an arc that bends inward. The lower parts of two adjacent third support poles 5 divided from two adjacent first support poles 4 are close together at the position which is 10-15 mm from the ends of the third support poles. The ends are slightly branched and splayed, the lower end 10 of which forms a subvertical support pole 10. The ends 6 of the support poles 5 are spherical round heads with the diameter of 35-65 mm contacting the blood vessel. When expanded, all support poles respectively stretch and form a filter net as a whole.

Embodiment 8: Animal Experiment

Aim of animal experiment: to evaluate the feasibility and the safety of a new vena cava filter; and to evaluate the retrieval performance at different time windows and the endothelialization degree of the filter surface, so as to determine the retrieval time window.

Experimental method: animal experiment (pre-test) time: 2 months

Animals for animal experiment: one sheep (about 40 kg)

Taking aspirin for 30 days after implantation, floating thrombus appeared in the vena cava, the iliac vein, under effective anticoagulant therapy.

At the end time, the degree of migrating of the vena cava filter was evaluated by angiography, and the animal was sacrificed after the filter retrieved by using a capture system.

Auxiliary equipment used during animal experiment: angiography machine.

Figure 7:
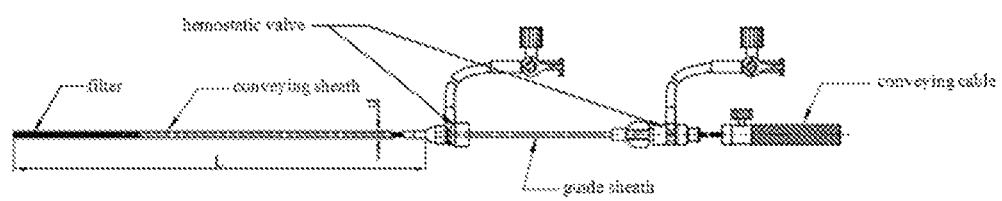
FIG. 7 is a schematic diagram of a push device used to implant the inferior vena cava filter of the invention.
Figure 8:
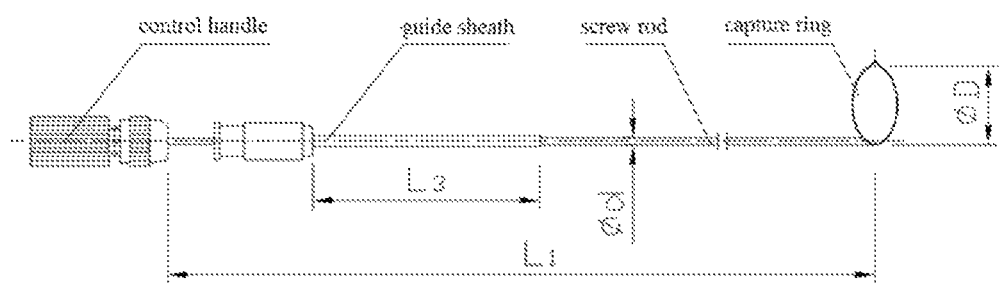
FIG. 8 is a schematic diagram of a capture system used to retrieve the inferior vena cava filter of the invention.

Under the condition of anesthesia, the animal signs were observed, using the angiography machine. The vena cava filter of embodiment 4 was conveyed with the push device shown in FIG. 7 to vena cava. At the end time, the vena cava filter was retrieved with the capture system shown in FIG. 8, by trapping the retrieval hook, then the endothelialization degree on the surface of the filter was observed.

Results and conclusions: the inferior vena cava filter of the embodiment can be used for temporarily placing in the inferior vena cava through the interventional method to prevent the thrombus formed in the veins of the lower extremity from ascending and causing pulmonary embolism. The implementation of the embodiment could prolong the temporary placement time of the inferior vena cava filter in the blood vessel, effectively prevent secondary pulmonary embolism and offer protection during the risk period of pulmonary embolism. After the risk period of thrombosis, the inferior vena cava filter could be removed successfully, so as to avoid permanent implantation of the inferior vena cava filter in the blood vessel and causing subsequent risks and complications of permanent implantation.

The structure of the inferior vena cava filter of the embodiment provides the filter with two layers of sites contacting the blood vessel. The design of multiple endpoints greatly reduced the contact area between the device and the inner surface of the blood vessel, converting the surface-to-surface contact into point-to-point contact, which made it difficult for the endothelial cell to attach. This can prolong the time of keeping the inferior vena cava filter in the blood vessel to 2~3 months and can be used for keeping the centering of the filter in the blood vessel.

The inferior vena cava filter of the embodiment had the structure of two layers of sites contacting the blood vessel, such that the filter had better self centering, and the filter was prevented from tilting after implantation.

The inferior vena cava filter of the embodiment was designed with multiple poles, which can easily extract the support poles from the endothelial tissue under the action of upward tension and is convenient for removing operation.

The animal experiments implemented by the inferior vena cava filters of other embodiments had similar preventive and therapeutic effects.

The above embodiments 1-7 are the implementation of the invention, but the implementation of the invention are not limited by the above embodiments. Any other alteration, modification, substitution, combination and simplification without departing from the spiritual essence and principle of the invention are all equivalent replacement methods included in the scope of protection of the invention.

The invention claimed is:

1. An inferior vena cava filter, comprising: a retrieval hook, a connecting part and a plurality of support poles,
   wherein the retrieval hook and the plurality of support poles are arranged on opposite sides of the connecting part;
   wherein the connecting part is provided with an internal component for connecting with a push device,
   wherein the plurality of support poles comprise a plurality of first support poles, each first support pole having a first end and an opposite second end, the first end secured to the connecting part,
   wherein two third support poles extend from the second end of each first support pole;
   wherein when expanded, two adjacent third support poles that extend from two adjacent first support poles are in contact but not connected to each other.

2. The inferior vena cava filter according to claim 1, wherein the plurality of first support poles are radially evenly spaced.

3. The inferior vena cava filter according to claim 1, wherein each first support pole has a length of 8-16 mm; and each third support pole has a length of 10-16 mm.

4. The inferior vena cava filter according to claim 1, wherein the inferior vena cava filter is formed by laser cutting of a nickel-titanium alloy tube.

5. The inferior vena cava filter according to claim 1, wherein the push device is a push rod, wherein a connection between the connecting part and the push rod is selected from the group consisting of a threaded connection, a buckle connection and a trap connection.

6. The inferior vena cava filter according to claim 1, wherein a second support pole extends from the second end of each first support pole.

7. The inferior vena cava filter according to claim 6, wherein the numbers of the first support poles and the second support poles are respectively between 4 and 8; and the number of the third support poles is between 8 and 16.

8. The inferior vena cava filter according to claim 7, wherein the number of the first support poles and the second support poles is respectively 6; and the number of the third support poles is 12.

9. The inferior vena cava filter according to claim 6, wherein each second support pole has a bent part having a length of 4-20 mm, a curvature radius of 3-10 mm, and a bending angle of 90-270 degrees.

10. The inferior vena cava filter according to claim 6, wherein each second support pole and each third support pole have a free end that is a spherical round head.

11. The inferior vena cava filter according to claim 6, wherein an expanded diameter of the second support poles is 5-10 mm larger than a diameter of a blood vessel which the inferior vena cava filter is to be deployed into, wherein an expanded diameter of the third support poles is 15-25 mm larger than the diameter of the blood vessel.

12. The inferior vena cava filter according to claim 6, wherein each second support pole is substantially straight.

13. The inferior vena cava filter according to claim 1, wherein a free end of each third support pole is not in contact with a free end of another third support pole.

14. The inferior vena cava filter according to claim 1, wherein the third support poles extend away from the first support poles, and wherein the third support poles are in contact with an inner wall of a blood vessel when the inferior vena cava filter is implanted in the blood vessel.

\* \* \* \* \*